United States Patent [19]

Tyhach

[11] Patent Number: 4,524,133

[45] Date of Patent: Jun. 18, 1985

[54] TEST DEVICE FOR LACTASE ACTIVITY IN A MECONIUM SAMPLE

[75] Inventor: Richard J. Tyhach, Elkhart, Ind.

[73] Assignee: Miles Laboratories, Inc., Elkhart, Ind.

[21] Appl. No.: 496,925

[22] Filed: Aug. 19, 1983

Related U.S. Application Data

[63] Continuation of Ser. No. 289,455, Aug. 3, 1981, abandoned.

[51] Int. Cl.³ .................... C12Q 1/54; C12Q 1/34; C12Q 1/26; C12Q 1/28
[52] U.S. Cl. ................................ 435/14; 435/18; 435/25; 435/28; 435/805; 422/56
[58] Field of Search ............... 435/4, 14, 18, 25, 26, 435/28, 805, 810; 422/56

[56] References Cited

U.S. PATENT DOCUMENTS

| | | | |
|---|---|---|---|
| 4,273,868 | 6/1981 | Walter | 435/14 |
| 4,279,993 | 7/1981 | Magers et al. | 435/14 |
| 4,385,114 | 5/1983 | Güthlein et al. | 435/14 |

OTHER PUBLICATIONS

Shwachman et al., Am. J. Dis. Child., 132:1112–1114 (1978).
Green et al., Pediatrics, 21:645–641 (1958).
Antonowicz et al., Pediatrics, 56:782–787 (1975).

*Primary Examiner*—Esther M. Kepplinger
*Attorney, Agent, or Firm*—Roger N. Coe

[57] ABSTRACT

A test device for the detection of lactase activity in a meconium sample is disclosed. The test device is a carrier matrix which has lactose, a glucose assay system and a nonionic detergent incorporated therein.

6 Claims, No Drawings

TEST DEVICE FOR LACTASE ACTIVITY IN A MECONIUM SAMPLE

This is a continuation of application Ser. No. 289,455, filed Aug. 3, 1981, now abandoned.

BACKGROUND OF THE INVENTION AND PRIOR ART

Cystic fibrosis (CF) is a genetic illness which has as its clinical features chronic pulmonary disease, pancreatic dysfunction and a high concentration of sodium and chloride in the sweat. Mucous plugs the pancreatic ducts, the intestinal mucous glands and the bronchial tree.

Studies have demonstrated raised levels of protein, predominately albumin, in meconium from infants with CF [See: *Pediatrics*, 21:635-641 (1958)]. A test device for the detection of albumin in meconium greater than 20 milligrams per gram (mg/g) dry weight of meconium has been developed. [See *Pediatrics*, 55:35-38 (1975)]. Such test devices suffer from a failure to detect all newborns with CF, i.e. low sensitivity, and an unacceptable number of false-positives, i.e., low specificity. Because of the emotional stress caused by a false-positive test result for CF, reduction in the number of false-positive test results in a CF test is desirable.

*Pediatrics*, 56:782-787 (1975) reported an increase in disaccharidase activities in meconium from infants with CF and suggested measurement of lactase activity as well as the other activities, as a CF diagnostic test. *Am. J. Dis. Child.*, 132: 1112-1114 (1978) describes a study which included an assay test for lactase and β-D-fucosidase activity in conjunction with an assay for albumin, in meconium. The authors suggest that the addition of the lactase and fucosidase assay would reduce the occurrence of false-positive test results.

The lactase activity test described above involved a liquid assay test. The meconium sample was placed in a test tube and a 3 percent lactose solution in a maleate buffer added. After incubation for a period of 15 minutes, lactase activity was detected by the presence of glucose, demonstrated by immersing a glucose reagent strip into the mixture and after 10 minutes, examining the glucose reagent strip for a blue color (positive test).

Use of a liquid assay test system for lactase activity detection in meconium samples is inconvenient. Because the meconium sample is a tarry-like mass, the sample must be first homogenized. As described in *Am. J. Dis. Child.*, supra, the sample is homogenized with vigorous agitation in a buffer solution. Other workers have resorted to ultrasonic techniques to obtain homogenization. In order to properly prepare the sample for testing, the sample must be incubated for a period of from 15 minutes to one hour. In addition, the liquid assay test system requires the preparation of solutions for individual tests. In order to encourage greater screening for CF in infants, a more convenient test system is required, preferably a dip-and-read reagent strip. The present invention is directed to such a dip-and-read test device.

SUMMARY OF THE INVENTION

The present invention is directed to a device for detecting lactase activity in a meconium sample. The device is a carrier matrix impregnated with lactose, a glucose assay system, and a nonionic detergent.

DETAILED DESCRIPTION OF THE INVENTION

The test device can be prepared as elongated sheets of carrier material which have been incorporated with lactose, a glucose assay system and a nonionic detergent. These elongated sheets may take the form of bulk rolls, such as of filter paper material. The device is prepared by incorporating a carrier with a solution containing lactose, a glucose assay system and a nonionic detergent, and thereafter drying the impregnated carrier. The term carrier refers to matrices which are insoluble in and maintain their structural integrity when exposed to physiological or other liquids. Suitable matrices which can be used include paper, cellulose, wood, synthetic resin fleeces, glass fiber, nonwoven and woven fabrics, gelatin, various organic polymers, such as polypropylene, and other organic materials well known as film formers to those skilled in the art. Alternatively, the carrier may take the form of a pressed or molded tablet containing conventional carrier material. For convenience, the carrier can be suitably attached to an insoluble support or handle member which can be made from polystyrene. Incorporation of the carrier with the lactase-detecting solution can be effected by suitable techniques, such as by impregnating, printing or spraying the test composition onto the carrier.

From about 1 to 4 percent by weight of lactose is present. A preferred amount is about 3 percent by weight. The glucose assay system includes a 3,3',5,5'-tetraalkylbenzidine indicator, wherein alkyl is a $C_1$-$C_4$ alkyl; 3,3',5,5'-tetramethylbenzidine is preferred. Others which can also be used include 3-methyl, 3'-methyl, 5-ethyl, 5'-ethyl benzidine and 3,3',5,5'-tetraethylbenzidine.

The glucose assay system includes glucose enzymes which will react with glucose, produced by conversion of lactose to glucose by lactase present in meconium to produce a predetermined reaction product, such as hydrogen peroxide. For example, glucose oxidase obtained from molds can be used.

Preferably, a dual enzyme system is present: one enzyme transforms glucose to produce hydrogen peroxide, whereas the other enzyme has peroxidative activity. Substances having peroxidative activity which are useful in the present invention can be chosen from various organic and inorganic sources. Plant peroxidases, such as horseradish peroxidase or potato peroxidase, can be used. Inorganic compounds having peroxidative activity include iodides, such as sodium and ammonium iodides, and molybdates, such as potassium and ammonium molybdates. In addition, urohemin and a number of other porphyrin substances having peroxidative activity can be used. Other substances which are not enzymes, but which have peroxidative activity include such compounds as iron sulfocyanate, iron tannate, ferrous ferrocyanide, potassium chromic sulfate and the like.

Other glucose assay systems known to those skilled in the art are usable in the present invention. For example, those using glucose dehydrogenase, which produce color in the presence of tetrazolium salts.

The detergent present in the composition is a nonionic detergent. The use of such a detergent in the formulation described enables the production of a test device which has increased sensitivity, e.g., in the presence of a lactase-containing meconium sample, the strip develops a positive color within 1 to 2 minutes. Nonionic detergents suitable for use in the present invention are alkanolamides, ethoxy alkanolamides, ethoxy phenols and ethoxy fatty alcohols.

The amount of nonionic detergent used can be in the range from about 0.1 to 1.0 percent by weight (w/v). A preferred amount is about 0.25 percent by weight. The presence of a greater amount of detergent may be deleterious to enzymes present in the test device.

The test device of the present invention has a high sensitivity for detection of lactase activity. The meconium sample can be tested with the test device without dipping in water. It is only necessary to smear a very thin film of meconium on the test device. If the sample has lactase activity, an easily visible blue color develops directly beneath the meconium.

An interpolymer of methylvinyl ether and maleic anhydride is also useful in the formulation of the lactase detecting test device of the present invention. One such interpolymer is marketed commercially as Gantrez AN-139 by GAF New York, New York. When this interpolymer is dissolved in an alcohol it forms a partial ester derivative, and when the interpolymer is dissolved in water if forms an acid derivative. Since test means prepared in accordance with the present invention are typically prepared from aqueous alcohol solutions, test compositions in the final product will contain either an acid derivative or a partial ester derivative or a mixture of said derivatives. The presence of the above described interpolymer derivatives along with polyvinyl pyrrolidone (PVP) having, for example, an average molecular weight of about 40,000, greatly enhances the color formed when color forming indicators are oxidized by hydrogen peroxide in the presence of peroxidase. This enhancement of color aids in detecting the presence of glucose produced by the conversion of lactose to glucose, and hence a positive indication of lactase activity, in the meconium sample.

Horseradish peroxidase and glucose oxidase used in the example were obtained from the Research Products Division, Miles Laboratories, Inc., Elkhart, Indiana. A copolymer of methyl vinyl ether and maleic anhydride (Gantrez AN-139) and polyvinyl pyrrolidone (PVP) were obtained from GAF. The solvent used in preparing the solutions can be water, physiological solutions, organic solvents, such as methanol, or mixtures thereof.

EXAMPLE 1

Dip-and-read test devices for the detection of lactase activity were prepared using a two-step impregnating procedure. A first solution was prepared by mixing together the substances shown in Table 1 below.

TABLE 1

| Component | Amount | Final Concentration in Dip |
| --- | --- | --- |
| (w/v) polyvinylpyrrolidone (PVP)* | 30.0 milliliter (ml) | 3.0% |
| 1.37 M Citrate Buffer, pH 5.0 | 15.0 ml | 0.20% |
| poly(methylvinyl ether maleic anhydride) 10% (w/v) | 7.5 ml | 0.75% |
| polyethoxy oleyl** alcohol 10% (w/v) | 2.5 ml | 0.25% |
| Glucose Oxidase (4878 IU/ml) | 1.8 ml | 87.8 international units per milliliter (IU/ml) |
| Peroxidase (153 U/mg) | 50.0 milligrams (mg) | 0.5 mg/ml |

TABLE 1-continued

| Component | Amount | Final Concentration in Dip |
| --- | --- | --- |
| Lactose | 3.0 grams (g) | 3.0% |
| 20% w/v Ascorbic acid*** | 10 microliter (μl) | 0.002% |
| Distilled Water | to bring volume to | 100 ml |

*A PVP commercially available from GAF under the trade designation K29-32.
**A polyethoxylated fatty alcohol commercially available from GAF under the trade designation ON 870.
***Added to reduce oxidized indicator which forms as a result of peroxide contaminants in the PVP. Amount to add determined by titration of the dip to the equivalence point.

A sheet of Whatman 54 filter paper was impregnated to saturation with this impregnating solution and dried at 50°–55° C. for about 15 minutes. The impregnated sheet was then impregnated to saturation with a 5 millimolar (mM) solution of 3,3',5,5'-tetramethylbenzidine in acetone containing 0.1 percent ON-870, and dried at 50°–55° C. for one minute.

The paper so prepared was cut to 0.2 centimeter (cm)×0.4 cm to form test devices. The devices were then backed with double-faced adhesive tape and fixed thereby to polystyrene support members. Test devices were evaluated in two formats. In the first, a thin-layer of meconium was smeared on the test device. Care was taken to remove all excess by scraping the test device with a spatula. A pathological meconium sample, known to have high lactase activity showed blue color development where it was in contact with the test device, within ten seconds. Apparently, enough water is present in the meconium for the enzymatic reaction to occur in the test device.

In the second format, a drop of water was placed on the test device after application of the meconium. This served to enhance color development.

As a control, a meconium sample, known to have no lactase activity was tested with the test device of the present invention. The test was negative for lactase activity.

Accordingly, the tests of this example showed that the test device of the invention is capable of detecting lactase activity in a meconium sample accurately, quickly and easily.

What is claimed is:

1. A test device for the detection of lactase activity in a meconium sample which comprises a carrier matrix incorporated with a composition comprising 1 to 4 percent by weight lactose, 3,3',5,5'-tetraalkylbenzidine indicator, glucose oxidase, and 0.1 to 1 percent by weight of a nonionic detergent.

2. The test device of claim 1 in which the composition incorporated into the carrier matrix also contains peroxidase.

3. The test device of claim 1 in which the nonionic detergent is polyethoxy fatty alcohol.

4. The test device of claim 1 in which the carrier matrix is attached to a polystyrene substrate.

5. The test device of claim 1 in which the composition also contains an interpolymer of methylvinylether and maleic anhydride.

6. Test device for detection of lactase activity in a meconium sample which comprises a carrier matrix incorporated with a composition comprising 1 to 4 percent by weight lactose, 3,3',5,5'-tetramethylbenzidine, glucose oxidase, peroxidase, 0.1 to 1 percent by weight polyethoxy oleyl alcohol, an interpolymer of methylvinylether and maleic anhydride and polyvinyl pyrrolidone.

* * * * *